United States Patent [19]

Kerkenaar

[11] Patent Number: 4,814,331

[45] Date of Patent: Mar. 21, 1989

[54] METHOD FOR CONTROLLING VASCULAR WITHERING DISEASES IN PLANTS, ESPECIALLY DUTCH ELM DISEASE

[75] Inventor: Antonius Kerkenaar, Blaricum, Netherlands

[73] Assignee: Nederlandse Organisatie Voor et al., The Hague, Netherlands

[21] Appl. No.: 779,822

[22] Filed: Sep. 25, 1985

[30] Foreign Application Priority Data

Sep. 28, 1984 [NL] Netherlands .................. 8402979

[51] Int. Cl.$^4$ .................. A01N 43/84; A01N 43/60; A01N 43/64; A01N 43/50
[52] U.S. Cl. .................. 514/231.5; 514/231.2; 514/255; 514/256; 514/277; 514/352; 514/383; 514/384; 514/396; 514/399
[58] Field of Search .................. 514/227, 231.5, 231.2, 514/255, 256, 277, 352, 383, 384, 396, 399

[56] References Cited

U.S. PATENT DOCUMENTS

3,686,399  8/1972  Sanne et al. .................. 514/227

FOREIGN PATENT DOCUMENTS

0014999  9/1980  European Pat. Off. .................. 514/227

OTHER PUBLICATIONS

Chem. Abst. 70:67075(s) (1969)–Pommer et al.
Chem. Abst. 88:1376(f) (1978)–Roka et al.
Chem. Abst. 88:184437(n) (1978)–Buchenauer.
Chem. Abst. 92:123,167(s) (1980)–Bohner et al.
Chem. Abst. 93:90010(a) (1980)–Prasad et al.
Chem. Abst. 98:104367(q) (1983)–Schmitt et al.
Chem. Abst. 99:35992(w) (1983)–Bladocha et al.
Chem. Abst. 100:19154(h) (1984)–Goebel.
Chem. Abst. 100:46864(w) (1984)–Gendle et al.
Chem. Abst. 101:2216(c) (1984)–Jordow et al.
Chem. Abst. 102:19535z (1985)–Hosokawa.
Effects of Fenpropimorph and of Tridemorph on Growth of Maize Seedlings; Amer. Proc. Phytochems Soc. Eur., vol. 24, 1984; Pierre Benveniste et al.
Effects of Triarimol, Tridermorph and Triparanol on Sterol Biosynthesis in Carrot, Tobacco and Soybean Suspension Cultures; Hosokawa et al.; Lipids, vol. 19, No. 6, pp. 449–451 (1984).
C. L. Wilson et al., "New Injection Equipment and a New Fungicide for Dutch Elm Disease Control", Biological Abstracts, vol. 65, No. 7, Jan. 1978, p. 420, & Plant Dis. Rep., 61(8), pp. 694–698, 1977.
R. Prasad et al., Commonwealth Agricultural Bureau, 1978, Summary 78204998, & Information Report, Chemical Control Research Institute, Canada, No. CC-X-125, 1976, pp. 1–17.
H. Buchenauer et al., Commonwealth Agricultural Bureau, 1974, Summary 74742326, & Plant Disease Reporter, part 57, No. 5, May 1973, pp. 460–462.
C. R. Clifford et al., "The Control in Vitro of Ceratocyctis Ulmi by Amine Cations", Chemical Abstracts, vol. 85, No. 15, Oct. 11, 1976, p. 169, Summary 105217j, & Pestic. Sci., 1976, 7(1), pp. 86–90.
H. Buchenauer, "Mode of Action and Selectivity of Fungicides which Interfere with Ergosterol Biosynthesis", Chemical Abstracts, vol. 89, No. 25, Dec. 18, 1978, p. 160, Summary 210265d & Proc. Br. Crop Prot. Conf.-Pest. Dis., part 3, 1977, pp. 699–711.
Med. Fac. Landbouww., Rijksuniversiteit Gent, 44/2, 1979, pp. 487–497.

Primary Examiner—Douglas W. Robinson
Attorney, Agent, or Firm—Brumbaugh, Graves, Donohue & Raymond

[57] ABSTRACT

Method for controlling vascular withering diseases in plants, especially trees, such as controlling Dutch elm disease by a propylactic or curative treatment of plants with a systemic fungicide which inhibits sterol biosynthesis.

4 Claims, No Drawings

METHOD FOR CONTROLLING VASCULAR WITHERING DISEASES IN PLANTS, ESPECIALLY DUTCH ELM DISEASE

The invention relates to a method for controlling vascular withering diseases in plants, in particular trees, by prophylactic or curative treatment of the plants with a systemic fungicide.

Vascular withering diseases, which are caused by dimorphous or polymorphous fungi, occur in various plants and normally lead to the death of the affected plant. Alongside vascular withering diseases in, for example, tomato and oak, the occurrence of Dutch elm disease causes great concern since this disease has now assumed world-wide proportions. Dutch elm disease is caused by a dimorphous fungus, *Ophiostoma ulmi,* also called *Ceratocystis ulmi.* This dimorphous fungus can occur both in the yeast form and the mycelium form. The spread of the fungus from woody vessel to woody vessel in the tree can occur exclusively when the fungus is in the mycelium form. In the course of the disease process, the fungus grows principally in the woody vessels and travels via the membrane which forms the connection between the woody vessels, from one woody vessel to the other. In the woody vessels, the fungus forms conidia which are carried along by the stream of sap by which means the fungus can spread rapidly through the tree. Under the influence of metabolites produced by the fungus, such as toxins, growth factors and enzymes, the tree reacts by forming gum and tylose in the vessels, as a result of which there is serious impediment to the water transport and withering of the leaves occurs. In the case of serious attack the cambium dies off and the tree becomes dead.

In North-West Europe Dutch elm disease is principally spread by the large elm bark beetle (*Scolytus scolytus*) and the small elm bark beetle (*Scolytus multistriatus*). In the United States of America and in Canada there is yet another beetle (*Hylurgonipus rufipes*) responsible for the spread of Dutch elm disease. Moreover, elms growing close to one another can be connected to one another by the roots, and the fungus can travel from one tree to the other by this means. In addition to the abovementioned dimorphous fungus of the family of Ophiostomataceae, namely *Ceratocystis ulmi,* there may also be mentioned *Ceratocystis fagacearum.* Other fungi which cause vascular withering diseases in plants are, for example, varieties of Verticillium from the class of the Hyphomycetes, such as *Verticillium alboatrum* and *V. dahliae.*

The controlling of vascular withering diseases such as Dutch elm disease is mainly based on removing and destroying the affected plants such as the affected elm trees, severing underground root connections, controlling beetles, responsible for the spread of the vascular withering diseases, by means of insecticides, and controlling the fungi themselves by means of fungicides.

A great deal of research has been devoted to the effectiveness of certain benzimidazole-2-yl-carbamates in controlling *Ophiostoma ulmi.* These are systemically active fungicides which spread more or less completely through the entire tree. As compounds used for this purpose there may above all be mentioned benomyl, namely 1-(butylcarbamoyl)-benzimidazole-2-yl-carbamic acid methul ester, MBC or Carbendazim, namely benzimidazol bamic acid methyl ester, and thiophanate-methyl, namely 1,2-bis-(3-methoxycarbonyl-2-thioureido)-benzene. In the case of both benomyl and thiophanate-methyl it is assumed that the substance active in an aqueous medium is benzimidazole-2-yl-carbamic acid methyl ester. Further, 1-methoxycarbonyl-3-(2-dimethylamino-acetamidophenyl)-thiourea-HCl and thiabendazol, namely 2-(4-thiazolyl)-benzimidazole and the water-soluble hypophosphite thereof have been used to control *O. ulmi.* Benomyl and thiabendazole are the fungicides most extensively used for this purpose.

These systemically active fungicides can be employed in various ways. Initially, these substances were used by moistening the root zone of the trees with a solution of the fungicide. In general, the fungicide is taken up efficiently by the roots but for effective control large quantities have to be employed, amounting, for example, to more than 40 $g/m^2$ in the case of benomyl. This method of use has been abandoned since it threatened excessive danger to the environment through, for example, damage to other organisms in the soil.

Spraying of leaves, branches and trunks of the trees, especially of large trees in towns, is extraordinarily difficult to carry out, though some success has been achieved therewith. The currently most widely used method is the injection of roots, root stumps and especially the trunk of elms with a solution of a systemic fungicide. In this method, again, high concentrations have to be used in order to achieve a satisfactory effect. High fungicide concentrations are, however, not tolerated well by elm trees. Moreover, *O. ulmi* appears to develop resistance to the fungicides hitherto employed.

Moreover, "Biological Control of Dutch Elm Disease by Pseudomonas Species" by R. J. Scheffer, Ann. Appl. Biol. (1983) 103 pages 21–30) discloses a method for controlling or preventing Dutch elm disease. According to this method, elm trees are to some extent protected against *Ophiostoma ulmi* if the trees, before infection (preventive treatment) are injected by means of a gauge pistol with a bacterium isolate of the species Pseudomonas. When, however, the infection with *Oohiostoma ulmi* has already taken place, the injection of the elm trees with a bacterium isolate of the species Pseudomonas as a curative treatment frequently offers hardly any solace.

It has now been found that fungicides which inhibit sterol biosynthesis can be successfully employed for controlling vascular withering diseases in plants, especially for controlling Dutch elm disease. In fact, sterol biosynthesis inhibitors appear to act, even in very low doses, on, for example, *O. ulmi* in such a way that this dimorphous organism can no longer exist in the mycelium form but solely in the yeast form. Since the mycelium form is necessary for the spread of *O. ulmi,* it is possible to control, for example, Dutch elm disease effectively by means of this class of fungicides.

The present invention thus relates to controlling vascular withering diseases in plants, caused by dimorphous or polymorphous fungi, by means of sterol biosynthesis inhibitors. The method according to the invention can, if desired, be combined with the abovementioned bacteriological control of *Ophiostoma ulmi* according to R. J. Scheffer.

The sterol biosynthesis inhibitors which can be used in the method according to the invention belong to various chemical categories and can therefore not be defined in terms of a general formula encompassing all compounds. Whether a chemical compound belongs to the sterol biosynthesis inhibitors can be determined in a simple manner, as follows:

*O. ulmi* is cultured in a defined glucose/salts medium with arginine as the nitrogen source, as described by Kulkarni and Nickerson (Exp. Mycol. 5 (1981), 148–154). The abovementioned medium is inoculated with a conidio spore inoculum, causing the fungus to grow in the mycelium form. Various concentrations of the chemical compound to be examined are then used in order to investigate whether, and at what concentration, the fungus is no longer capable of growing in the mycelium form but only in the yeast form. The chemical compound to be tested is, for this purpose, added to the medium in a series of concentrations in a suitable solvent (ethanol, acetone, DMSO or distilled water) in order to obtain the correct concentration in the medium. From evaluation of the measurements thus obtained it is possible to deduce whether the chemical compound tested is a sterol biosynthesis inhibitor and at what concentration it is active.

The use of all compounds known as sterol biosynthesis inhibitors, and also of preparations based thereon, for controlling vascular withering diseases in plants, especially for controlling Dutch elm disease, falls within the scope of the invention. A survey of the sterol biosynthesis inhibitors already examined for control of fungi, especially of ergosterol biosynthesis inhibitors, is given by A. Fuchs and M. A. de Waard in "Fungicide Resistance in Crop Protection" by J. Dekker and S. G. Georgopoulos, Pudoc, Wageningen 1980, pages 71–86 and 87–100. Sterol biosynthesis-inhibiting fungicides which can be used according to the invention include:

Triforine, having formula 1

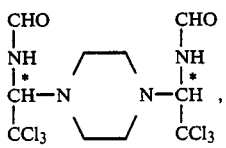

a compound containing a piperazine ring, dodemorph (formula 2)

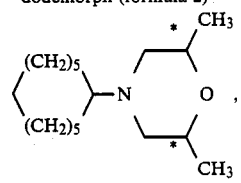

fenpropimorph (formula 3)

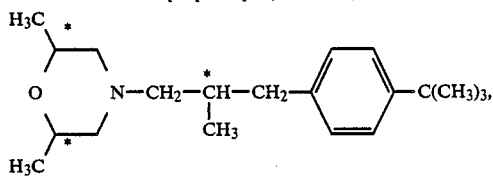

and tridemorph (formula 4)

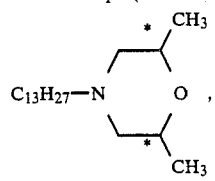

compounds possessing a morpholine ring, and buthiobate (formula 5)

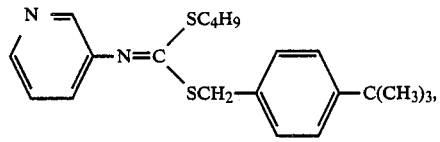

EL-241 (formula 6)

and fenpropidine (formula 28)

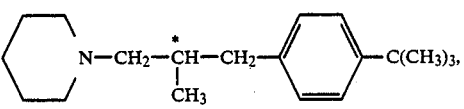

compounds possessing a pyridine ring, the pyrimidine compounds ancymidol (formula 7)

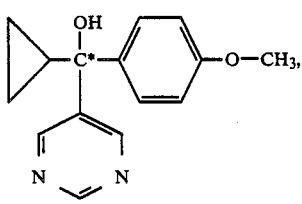

fenarimol (formula 8)

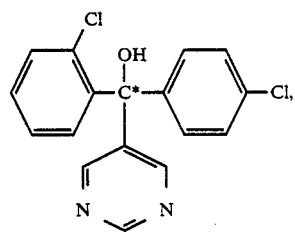

nuarimol (formula 9)

and triarimol (formula 10)

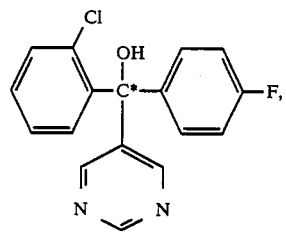
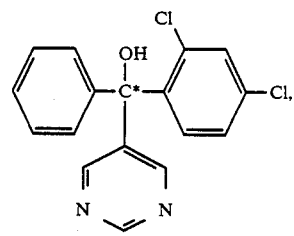
the imidazole compounds clotrimazole (formula 11)
N—dodecylimidazole (formula 12)
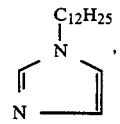
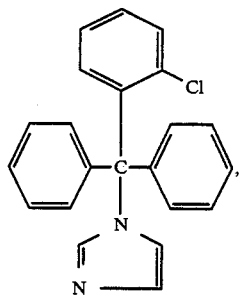
econazol (formula 13)
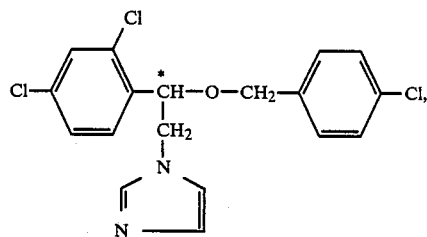
ketoconazole (formula 14)
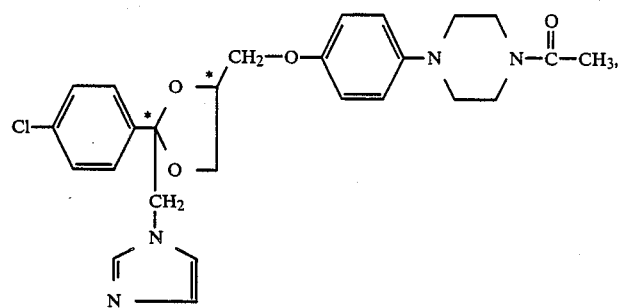
XE 326 (formula 15)
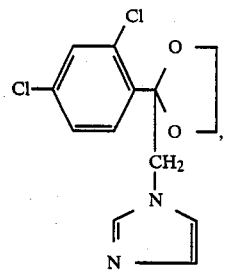
miconazole (formula 16)
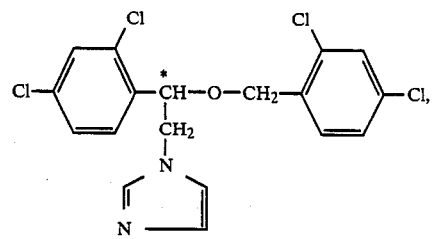
prochloraz (formula 18)

phenapronil (formula 17)

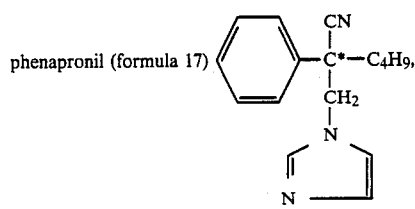

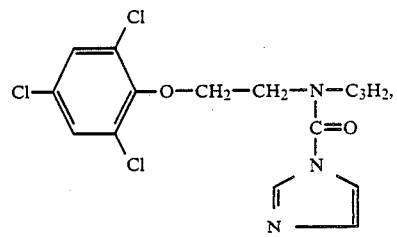

triflumazole (formula 19)

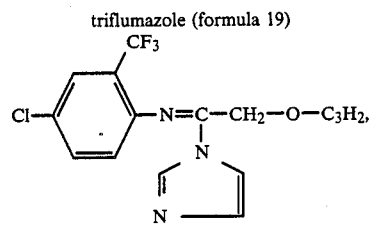

and imazalil (formula 20)

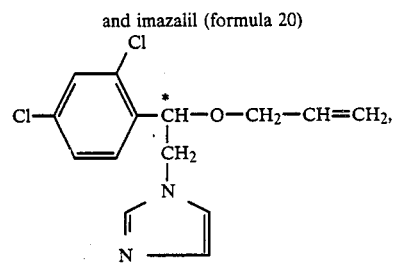

and the triazole compounds bitertanol (formula 21)

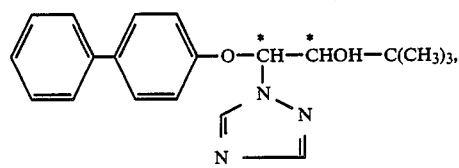

CGA 64250, also called propiconazole (formula 22)

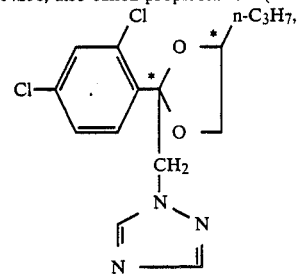

CGA 64251, also called etaconazole (formula 23)

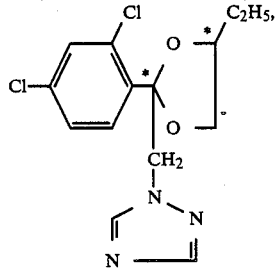

fluotrimazole (formula 24)

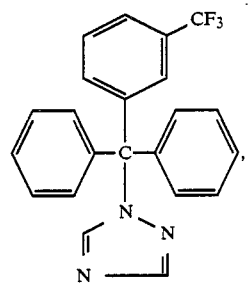

triadimefon (formula 25)

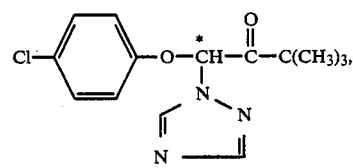

triadimenol (formula 26)

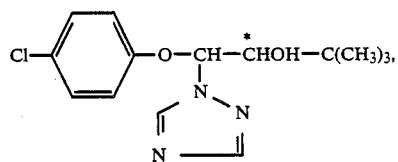

dicyclobutrazole (formula 27)

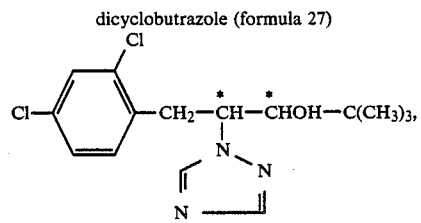

and S 3308 (formula 29)

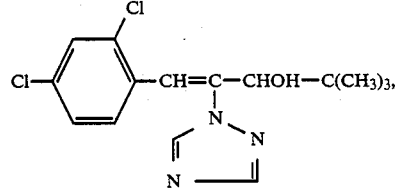

Exceptional results have been obtained with fenpropimorph and tridemorph as morpholine compounds, with prochloraz, triflumazole and imazalil as imidazole compounds and with propiconazole and etaconazole as triazole compounds. These compounds are employed preferentially in the method according to the invention.

The method according to the invention for controlling, for example, Dutch elm disease is carried out in a conventional manner, in general by treating, for example, elms which are in danger of becoming infected by *O. ulmi*, or already infected elms, with the sterol biosynthesis-inhibiting fungicides in such a manner that the fungicide is taken up by the elms. Since the quantities which are adequate to prevent *O. ulmi* from developing in the mycelium form are in general much lower, for example by a factor of 100, than the concentrations of the systemic fungicides hitherto used for controlling Dutch elm disease, the treatment of the elm trees can be carried out without problems. In this context it is noted that the treatment of the root zone of the trees with the sterol biosynthesis inhibitors to be employed according to the invention presents hardly any problems concerning the surrounding environment. Good results are also obtained by injecting elms with solutions or suspensions of the agents according to the invention. In this method the concentration of active substance can be substantially lower than in the case of the known systemic fungicides used for controlling Dutch elm disease, such as benomyl and thiabendazole.

The preparations to be employed for controlling vascular withering diseases in plants, especially Dutch elm disease, in accordance with the invention, and which also fall under the scope of the invention, can possess any desired form provided the active substance can be absorbed therefrom by the tree.

Determination of the EC-50 and MIC Values of the Compounds to be Used According to the Invention There follows below a description of the in vitro tests by means of which the EC-50* and MIC** values of the compounds to be used according to the invention are determined.

*The EC-50 value is the effective concentration in 50% growth inhibition (a concentration at which growth is 50% inhibited relative to the control).
**The MIC value is the minimal inhibitory concentration (the lowest concentration at which no microscopically perceptible growth occurs).

The in vitro tests were carried out with 2 strains of *O. ulmi*, namely an aggressive strain (H 6) and a non-aggressive strain (TX 21). These strains are described in an article by R. Sveldi and D. Elgersma in Eur. J. For. Path. 12 (1982), 29–36.

The MIC values and EC-50 values were determined by measuring the spread of the fungus on Petri dishes containing malt agar as the nutrient medium ("OX-OID" malt extract 3%, $K_2HPO_4$ 0.4%, $KH_2PO_4$ 0.1%, "Difco" agar 1.5%). The dishes were inoculated with a piece of infected agar obtained from a dish where the fungus had grown for 8 days. The inoculum piece was cut by means of a sterile cork borer (diameter 4 mm), under sterile conditions, from the edge of the colony and placed with the infected face on the dish to be inoculated. Incubation was carried out at 24° C. in a dark place.

The inhibitors were added to the still just liquid agar medium by means of, of solutions, of graded concentration, in acetone, ethanol or distilled water, the final concentration of solvent being at most 1%. The relevant solvent was added to the blank sample. Thereafter the liquid was poured into Petri dishes and after it had gelled the dish was inoculated in the manner described above.

The concentration range of each substance was between 0.05 and 50 ug/ml with successive steps of 0.05, 0.1, 0.2, 0.5 and so on. The EC-50 and MIC values were determined 14 days after inoculation.

The results of the EC-50 and MIC determinations are shown in Table A below.

TABLE A

EC-50 and MIC determinations in ug/ml on malt agar:
pH about 6.5; 14 days; 24° C.
(colony diameter of the control 7-8 cm)

|  | H6 EC-50 | TX 21 EC-50 | H6 MIC | TX 21 MIC |
|---|---|---|---|---|
| morpholines: | | | | |
| fenpropimorph | <0.05 | <0.05 | 0.2 | 2 |
| tridemorph | <0.05 | <0.05 | 20(50) | 20(50) |
| pyrimidines: | | | | |
| fenarimol | 0.2-0.5 | 0.1-0.2 | >50 | 50 |
| nuarimol | 0.2-0.5 | 0.2-0.5 | ≧50 | ≧50 |
| imidazoles: | | | | |
| clotrimazole | 0.5-1 | 1-2 | >50 | >50 |
| miconazole nitrate | 0.1-0.2 | 0.05-0.1 | 50 | 20(50) |
| prochloraz | 0.05-0.1 | <0.05 | 5 | 5 |
| imazalil sulphate | 0.05 | <0.05 | 2 | 1 |
| triazoles: | | | | |
| bitertanol | 5-10 | 10 | >>50 | >>50 |
| triadimefon | | | | |
| diclobutrazole | 0.5-1 | 0.5-1 | >50 | >50 |
| triadimenol | 0.5-1 | 0.5-1 | >50 | >50 |
| propiconazole CGA 64 250 | 0.05-0.1 | <0.05 | 20 | 10 |
| etaconazole CGA 64 251 | 0.05 | ≦0.05 | 10 | 5 |
| piperazine: | | | | |
| triforine | 5-10 | 1-2 | >>50 | >>50 |
| imidazole: | | | | |
| triflumazole | <0.05 | <0.05 | 5-10 | 10-20 |

FIELD TESTS (A) Test Trees

In the field tests, the following varieties of elm, sensitive to Dutch elm disease, were used:
*Ulmus Hollandica* x *Belgica* (HB)
*Ulmus americana* (Ua)

The elms used for the tests were divided into the three following size categories:

|  | Height | Trunk girth |
|---|---|---|
| "small" (HB) | approx. ½–1 m | 3–4 cm (measurement height 10 cm) |
| "medium" (HB) | approx. 2–3½ m | 10–15 cm (measurement height 10 cm) |
| "large" (Ua) | approx. 4–8 m | 24–60 cm (measurement height 50 cm) |

(B) Inoculation

In the tests according to the invention, the elms were inoculated with the aggressive strain *C. ulmi* H6. This inoculation was carried out with injection liquids which were obtained by filtering a fully developed shaken culture thereof in Tchernoff's medium (3–7 days, room temperature) through glass wool, washing it once in sterile tap water (centrifuging for 10 minutes at about 8000 g) and diluting it to $5 \times 10^5$ conidia per ml (see Ann. Appl. Biol. (1983) 103, pages 21–30). For the inoculation, a healthy upward growing branch in the uppermost part of the tree was chosen. A small chisel was driven into the branch a few centimeters above the base of the branch, and 20 ul of conidia suspension were applied.

The following inoculation operations were carried out for the abovementioned size categories of the elms:

For size category "small" 1 inoculation was carried out in one branch.

For size category "medium", 2 inoculations were carried out in one branch.

For size category "large", 2 inoculations per branch were carried out in 4 branches.

(C) Application of Fungicide

In the tests according to the invention, fenpropimorph or a preparation called Corbel (a spray preparation of fenpropimorph; 75% active substance) was employed after dilution with tap water (sterile, except in the case of pressure injection).

For trees of size categories "small" and "medium", the method of "absorption via the trunk wall" was employed. For this, a hollow chisel (8 mm wide) was forced into the tree to a depth of about 0.5 cm at a height of 5–10 cm, immediately after which 0.1–0.3 ml of fungicide solution was gradually fed to the tip of the chisel. This solution was normally absorbed by the tree within a few minutes. More especially, in the case of the small trees the fungicide was applied at 1 or 2 points and in the case of the trees belonging to the "medium" size category it was applied at 3 to 5 points depending on the diameter of the tree.

For the trees of the "large" size category, 0.5–1 liter of Corbel solution was injected. This injection was effected by pressure injection at a height of 20–30 cm, for which about 2 cm deep holes were drilled with an 8 mm drill over 6 to 8 cm of the girth of the tree. Hollow plugs (so-called "maple-leaf taps") were fitted into the holes obtained, and Corbel solution was injected via these plugs over 40 to 90 minutes under a pressure of 1–1.2 atmospheres gauge.

DISEASE DEVELOPMENT

After the inoculation and the application of fungicide, the development of the disease of the elms was assessed at regular intervals on the basis of the development of symptoms. For this, the following disease index was employed:
0: healthy, no symptoms;
1: yellowing of a number of leaves;
2: withering, yellowing and necrosis of a number of leaves; the tree is clearly affected;
3: withering, yellowing and partial necrosis of numerous leaves; more than 1 branch is affected;
4: serious withering and necrosis of most of the leaves; several branches are dead;
5: the tree is dead or virtually dead.

Tables B, C and D below show the results obtained in the tests according to the invention. From these tests it can be deduced that in the case of small elm trees (HB) a prophylactic fungicide treatment prevents infection with *O. ulmi*;

in the case of medium-sized elm trees (HB) the disease process can at least be halted with an adequate concentration of fungicide and in the case of the large elm trees (Ua), given an adequate amount of the sterol biosynthesis inhibitor according to the invention, a retardation of the disease process or a curative action can be found, relative to the control trees.

TABLE B

| (HB, small) | 21 days after inoculation | 46 days after inoculation |
| --- | --- | --- |
| Control (4×) 2 days before inoculation | 0, 1, 1½, 1½ | 1½, 3, 3½, 4 |
| 0.07 ml of Corbel | 0 | 0 |
| 0.07 ml of fenpropimorph | 0 | 0 |

TABLE C

| (HB, medium) | | |
| --- | --- | --- |
| Control | 21 days after inoculation | ±40 days after inoculation |
| A (3×) | 1, 2, 2 | 2, 2, 3 |
| B* (4×) | 1½, 1½, 3, 3 | 3, 4, 4, 4 |
| C** (3×) | 1, 1, 1½ | 4, 4, 4 |

| Corbel ml | days before (−) or after (+) inoculation | | | cf. control series |
| --- | --- | --- | --- | --- |
| 0.07 | −2 | 1½ | 4 | B* |
| 0.1 | −1 | 0.0 | 1.1 | A |
| 0.1 | +7 | 0 | 1 | C** |
| 0.2 | +14 | 1½, 2 | 1½, 1½ | A |

(*more heavily inoculated)
(**inoculated 1 week earlier)

TABLE D

| (Ua, large) | 21 days after inoculation | 38 days after inoculation | 42 days after inoculation |
| --- | --- | --- | --- |
| Control (5×) | ½, ½, 1, 1, 1 | 2, 2, 2, 3, 3 | 2½, 2½, 3½, 4, 4 |
| 0.25 ml of Corbel | 1 | 2 | 3 |
| 0.75 ml of Corbel | ½ | 1 | 2 |
| 5 ml of Corbel | ½ | 1 | 2 |
| 7 ml of Corbel | 0 | 0 | 0 |
| 10 ml of Corbel | 1 | 1 | 1 |
| 25 ml of Corbel | 0 | 0 | 0 |
| 25 ml of Corbel | 0 | ½ | 0 |
| 30 ml of Corbel | ½ | ½ | 0 |

I claim:

1. A method of controlling vascular withering diseases of plants caused by a dimorphous or polymorphous fungus which grows both in a yeast form and in a mycelial form comprising
administering to a plant in need of treatment a systemic fungicide which inhibits sterol biosynthesis in an amount that is effective to prevent growth of the fungus in the mycelial form but that allows growth of the fungus in the yeast form.

2. A method of controlling vascular withering diseases of plants caused by a dimorphous or polymorphous fungus which grows both in a yeast form and in a mycelial form comprising
administering to a plant in need of treatment a systemic fungicide which inhibits sterol biosynthesis in an amount that is effective to prevent growth of the fungus in the mycelial form but that allows growth of the fungus in the yeast form, said fungicide being selected from the group consisting of triforine, fenpropimorph, tridemorph, dodemorph, fenarimol, nuarimol, clotrimazole, miconazole, prochloraz, imazalil, triflumazole, bitertanol, triadinephon, dicyclobutrazole, triadimenol, propiconazole and etaconazole.

3. A method according to claim 2, wherein the systemic fungicide is fenpropimorph.

4. A method of controlling vascular withering diseases of plants caused by a dimorphous or polymorphous fungus which grows both in a yeast form and in a mycelial form comprising
administering to a plant in need of treatment a systemic fungicide which inhibits sterol biosynthesis in an amount that is effective to prevent growth of the fungus in the mycelial form but that allows growth of the fungus in the yeast form, said fungicide being selected from the group consisting of fenpropimorph, tridemorph and dodemorph.

* * * * *

UNITED STATES PATENT AND TRADEMARK OFFICE
CERTIFICATE OF CORRECTION

PATENT NO. : 4,814,331

DATED : Mar. 21, 1989

INVENTOR(S) : Antonius Kerkenaar

It is certified that error appears in the above-identified patent and that said Letters Patent is hereby corrected as shown below:

<u>First page, Item 73</u>, "et al." should read --Toegepast-Natuurwetenschappelijk Onderzoek--;

<u>First page, 3rd line of ABSTRACT</u>, "propylactic" should read --prophylactic--; and <u>Col. 8, (formula 26)</u>, that portion of the formula reading "O-CH" should read --O-$\overset{*}{C}$H--.

Signed and Sealed this

Twenty-third Day of January, 1990

Attest:

JEFFREY M. SAMUELS

*Attesting Officer*   *Acting Commissioner of Patents and Trademarks*